United States Patent [19]

Blöcker et al.

[11] Patent Number: 4,863,848

[45] Date of Patent: Sep. 5, 1989

[54] DOUBLE-STRANDED VECTOR AND PROCESS USING IT

[75] Inventors: Helmut Blöcker, Hamburg; Ronald Frank, Wolfenbüttel, both of Fed. Rep. of Germany; Guido Volckaert, Aarschot, Belgium

[73] Assignee: Gesellschaft fur Biotechnologische Forschung mbH (GBF), Braunschweig-Stockheim, Fed. Rep. of Germany

[21] Appl. No.: 849,031

[22] Filed: Apr. 7, 1986

Related U.S. Application Data

[63] Continuation of Ser. No. 492,597, May 6, 1983, abandoned.

[30] Foreign Application Priority Data

May 7, 1982 [DE] Fed. Rep. of Germany ....... 3217239
Sep. 10, 1982 [DE] Fed. Rep. of Germany ....... 3233689

[51] Int. Cl.$^4$ .......................... C12Q 1/68; C12N 15/00
[52] U.S. Cl. .......................................... 435/6; 435/91; 435/172.3; 435/320; 935/6; 935/77
[58] Field of Search ...................... 435/172.3, 68, 317, 435/320, 6, 91; 436/94; 935/76-78

[56] References Cited

U.S. PATENT DOCUMENTS 4,237,224 12/1980 Cohen et al. .......................... 435/68

OTHER PUBLICATIONS

Eckert, *Gene* 51:247–254, 1987.
Covarrubias, et al. *Gene* 13:25–35, 1981.
Davis et al., 1980, A Manuel for Genetic Engineering Advanced Bacterial Genetics, Cold Spring Harbor Laboratory, pp. 168–172, 226–229, 250.

*Primary Examiner*—Thomas G. Wiseman
*Assistant Examiner*—Thomas D. Mays
*Attorney, Agent, or Firm*—Kane, Dalsimer, Sullivan, Kurucz, Levy, Eisele and Richard

[57] ABSTRACT

The invention concerns a double-stranded recombinant DNA cloning vector comprising one single insertion site for foreign DNA and one or two labelling sites adjacent or approximate to said insertion site. In the instance of two labelling sites, said sites flank the insertion site. The labelling site(s) can be individually labelled in a fashion that results in the labelling of the 3' end of either strand. The use of the invention in a process affords the ability to individually label only one strand at the 3' end in a simplified method for base sequencing analysis.

6 Claims, No Drawings

DOUBLE-STRANDED VECTOR AND PROCESS USING IT

CROSS-REFERENCE TO RELATED APPLICATION

This application is a continuation of U.S. patent application Ser. No. 492,597 filed May 6, 1983, now abandoned.

BACKGROUND OF THE INVENTION

1. Field of the Invention

The invention relates to DNA sequencing.

2. Brief Description of the Prior Art

The sequence analysis of large DNA molecules is possible since the development of the Maxam-Gilbert and Sanger-Coulson methods. These methods are based on three main principles:

(1) The use of a labelled nucleoside triphosphate in vitro for the radioactive labelling of the polynucleotide at its 5' or 3' ends or therebetween;

(2) The use of a cutting technique on the polynucleotide to be sequenced to form four or more groups of fragments with a fixed common end;

(3) The use of a polyacrylamide gel electrophoresis in order to sort, according to length, molecules within the groups, and copy them.

The nucleotide sequence can then, by mutual comparison of the different fractionation patterns of the four groups, be read in the form of an autoradiograph of the polyacrylamide gel. Each individual analysis can produce the sequence of a DNA segment of 200 to 500 nucleotides. These individual segments are then classified by examining overlapping stretches or areas.

A sequence analysis depends chiefly on ease of production of the fragments, which are analysed in suitable form before the base-specific reactions. In the Sanger-Coulson method this problem is solved by subcloning random DNA fragments in vectors derived from bacteriophage M13 at an insertion site in the vicinity of a sequence specific to the vector, from which sequencing reactions proceed (primer initiated repair synthesis in the presence of dideoxytriphosphates). The single-strand DNA matrix can be isolated by simple manipulations.

By contrast, the Maxam-Gilbert method require one or more gel separation stages and fragment-specific enzymatic reactions for the introduction and separation of the radioactive labelling. Consequently, the strategy often depends on an already existing arrangement of restriction cleavage sites in order to reduce the number of individual analyses.

Plasmid subcloning systems similar to the M13 system have been developed in various laboratories. Their object is the use of chemical degradation sequencing of individual recombinant subclones of a DNA molecule that is to be sequenced. The basic feature of these sequencing vectors is that two restriction cleavage sites are in the vicinity of the subcloning site (insertion site). The site in closer proximity to the insertion is used for the labelling reaction, whilst the other site permits separation of the labelling. Thus two labelled fragments are formed. The smaller fragment is not removed and produces a non-readable sequence in the lower region of the sequencing gel. This loss of sequence information amounts to fewer than 30 nucleotides in all of the processes hitherto known. All of these processes still include at least two restrictions and one labelling reaction.

The object of the present invention is to introduce DNA to be sequenced, or fragments of DNA to be sequenced, into a double-stranded vector, which can be individually labelled in a simple manner. It is intended, therefore, that only one strand of the vector be labelled.

SUMMARY OF THE INVENTION

In accordance with the invention, a double-stranded vector is provided with an insertion site (a) for foreign DNA that occurs only once in the vector, and a labelling site (b) that occurs only once in the vector and can be individually labelled. This is preferably a labelling site of the following type:

|     |                    |              |
| --- | ------------------ | ------------ |
| (i) | $-X_{3'}$          | $YX^+-$      |
|     | $-X^+Y^+_{5'}$     | $X-$ or      |
|     | $-X_{3'}$          | $YZ-$        |
|     | $-X^+Y^+_{5'}$     | $Z^+-$ or    |
| (ii)| $-XMZ_{3'}$        | $N^+Z^+-$    |
|     | $-X^+M^+_{5'}$     | $Z^+NX-$ or  |
|     | $-XMZ_{3'}$        | $N^+Y-$      |
|     | $-X^+M^+_{5'}$     | $Z^+NY^+-$ or|
| (iii)| $-XM_{3'}$        | $NX^+-$      |
|     | $-X^+M^+_{5'}$     | $N^+X-$ or   |
|     | $-MX_{3'}$         | $X^+N-$ or   |
|     | $-M^+X^+_{5'}$     | $XN^+-$ or   |
|     | $-XM_{3'}$         | $NY^+-$      |
|     | $-X^+M^+_{5'}$     | $N^+Y-$ or   |
|     | $-MX_{3'}$         | $Y^+N-$ or   |
|     | $-M^+X^+_{5'}$     | $YN^+-$      | in which each of M and N represents a single nucleoside from the group adenosine, cytidine, guanosine and thymidine, $M^+$ and $N^+$ represent the nucleosides complementary to M and N, M is not the same as N, each of X, Y and Z represents one or more nucleosides from the group adenosine, cytidine, guanosine and thymidine, $X^+$, $Y^+$ and $Z^+$ represent the nucleosides complementary to X, Y and Z, the nucleosides or nucleoside combinations represented by X, Y and Z are not identical to one another and, in the case of type (i), Y is not the same as $Y^+$.

The double-stranded vector is a clonable circular DNA.

Preferably, the insertion site (a) and the labelling site (b) are directly adjacent to each other or are separated from each other by up to 1000, preferably up to 100 and, especially, up to 10, base pairs. The insertion site (a) may be one for the introduction of foreign DNA having protruding ends or blunt ends.

DETAILED DESCRIPTION OF THE PREFERRED EMBODIMENTS OF THE INVENTION

The procedure for sequencing foreign DNA is as follows:

A. foreign DNA to be sequenced is introduced into the insertion site (a) of the vector, B. the hybrid vector formed is cloned, C. the labelling site (b) of the cloned hybrid vector is cut, D. the resulting ends of the opened hybrid vector are supplemented in the presence of DNA polymerase and one or more of the triphosphates dGTP, dTTP, dCTP and dATP, one of the, or the, triphosphate(s) being labelled (for example radioactively), and consequently the hybrid vector is individually labelled, and E. the labelled opened hybrid vector is base-specifically degraded in a manner known per se and the products of the degradation are analysed in a manner known per se.

Naturally, overlapping DNA fragments that have been obtained by random disintegration of a larger DNA molecule can be used as foreign DNA in the process according to the invention.

In the vector according to the invention, the insertion site (a) serves a different function from the labelling site (b). Whilst the insertion site (a) is intended to receive DNA to be sequenced, the intended use of the labelling site (b) is the individual labelling of the opened hybrid vector.

The individual labelling of the hybrid vector in accordance with the invention is explained in detail diagrammatically by the following Example. Labelling site An example of such a vector is pCSV03, which is described in detail hereinafter.

In this embodiment of the invention, the procedure for sequencing foreign DNA is as follows:

1. each end of the foreign DNA to be sequenced is provided with an insertion site that corresponds to one of the two insertion sites (a) and (c) of the vector, 2. the foreign DNA developed in this manner is disintegrated to form fragments which can be exchanged for the DNA fragment resulting when the insertion sites (a) and (c) of the vector are cut, 3. the foreign DNA is exchanged for the DNA fragment cut out from between the two insertion sites (a) and (c) of the vector, 4. the hybrid vector formed is cloned, 5. the labelling site (b) of the cloned hybrid vector is cut,

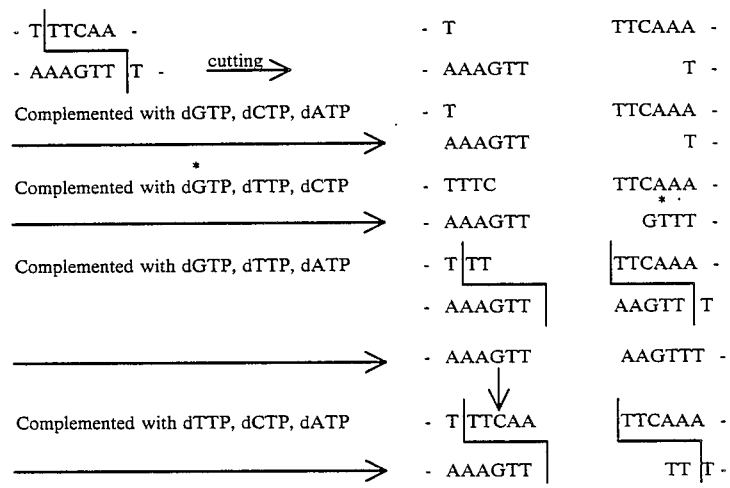

KEY:
G = guanosine, T = thymidine, C = cytidine, A = adenosine;
* = label.

From the Example given it can be seen that the skilled artisan can, on the basis of the nature of the labelling site, which is known to him, foresee with which labelled triphosphate, or with which combination of triphosphates and with which labelled triphosphate within the combination, he can achieve individual labelling at the given labelling site. In the Example given, this is the case with the triphosphate mixtures dGTP, dTTP and dC*TP or dG*TP, dTTP and dCTP.

In accordance with another embodiment of the invention, a double-stranded vector is provided with 1. an insertion site (a) for foreign DNA that occurs only once in the vector, 2. a labelling site (b), for example of the above-indicated type (i), (ii) or (iii), that can be individually labelled and occurs only once in the vector, and 3. an additional insertion site (c) for foreign DNA that occurs only once in the vector, and, on cutting, one of the two insertion sites (a) and (c) affords protruding ends and the other insertion site affords blunt ends. Preferably, the two insertion sites (a) and (c) are on the same side of the labelling site (b) and in the vicinity thereof. The insertion sites (a) and (c) are preferably directly adjacent to each other or are separated from each other by up to 1000, preferably up to 100 and, especially, up to 10, base pairs.

6. the resulting ends of the opened hybrid vector are supplemented in the presence of DNA polymerase and one or more of the triphosphates, dGTP, dTTP, dCTP and dATP, one of the, or the, triphosphate(s) being labelled (for example radioactively), and the hybrid vector is individually labelled, and 7. the labelled opened hybrid vector is base-specifically degraded in a manner known per se and the products of the degradation are analysed in a manner known per se. The feature of providing each end of the DNA to be sequenced with an insertion site that corresponds to an insertion site (a) or (c) (preferably for protruding ends) of the vector, is one wherein the two ends of the DNA to be sequenced are provided with a linker.

According to another embodiment of the invention, a double-stranded vector is provided with 1. an insertion site (a) for foreign DNA that occurs only once in the vector, 2. a labelling site (b), for example of the above-indicated type (i), (ii) or (iii), that occurs only once in the vector and can be individually labelled, and 3. an additional labelling site of the same type as the first labelling site (b) which occurs only once in the vector.

Preferably, the two labelling site (b) and (d) flank the insertion site (a) and are arranged in the vicinity thereof.

Preferably, the two labelling sites (b) and (d) are directly adjacent to the insertion site (a) or are separated therefrom by up to 1000, preferably up to 100 and, especially, up to 10, base pairs.

As already stated, the two labelling sites (b) and (d) should occur only once in the vector. It is, however, advantageous if they can be cut by the same restriction enzyme. The insertion site (a) may be one for the insertion of foreign DNA with protruding ends or with blunt ends.

The procedure for sequencing DNA with a vector of this arrangement is as follows:

1. DNA to be sequenced is introduced into the insertion site (a) of the vector,
2. the hybrid vector formed is cloned,
3. the two labelling sites (b) and (d) of the cloned hybrid vector are cut,
4. the two ends of the cut fragment with the incorporated foreign DNA are supplemented in the presence of DNA polymerase and one or more of the triphosphates dGTP, dTTP, dCTP and dATP, one of the, or the, triphosphate(s) being labelled, and on the one hand only one end of the cut fragment and on the other hand only its other end are individually labelled, and
5. the labelled cut fragment is base-specifically degraded in a conventional manner known per se and the products of the degradation are conventionally analysed for sequence in a manner known per se. The individual labelling according to the invention of the cut fragment with the incorporated foreign DNA is explained in detail diagrammatically by the following Example.

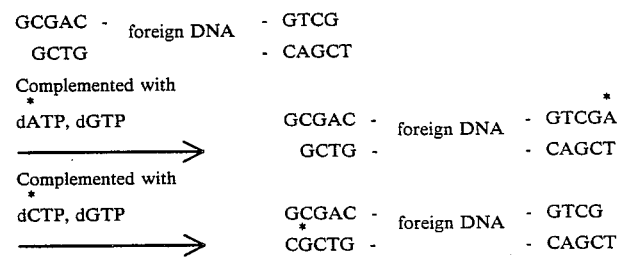

From the Example given it can be seen that the man skilled in the art can, on the basis of the nature of the labelling sites (b) and (d) which is known to him, foresee with which labelled triphosphate, or with which combination of triphosphates and with which labelled triphosphate within the combination, he can achieve individual labelling at one of the two labelling sites, The Example shows that either one or the other of the labelling sites can be individually labelled. Accordingly, in this embodiment of the invention both strands of the foreign DNA can be sequenced. The two strands can be completely sequenced thus increasing the reliability of the sequence analysis. However, it is also possible to sequence the two strands only as far as an overlapping area common to them; this procedure is advantageous especially when sequencing very long DNA strands.

To produce vectors according to the invention, the artisan must be able to sequence, cut and link DNA molecules. The known sequencing methods available to the artisan have already been mentioned. In addition, for cutting and linking DNA molecules, one may refer to German Pat. No. P 28 14 039.8 and the literature cited therein. Both the insertion sites (a) and (c) and the labelling sites (b) and (d) of the vectors according to the invention can be cut by restriction endonucleases, that is to say restriction enzymes. The skilled artisan is also familiar with the random disintegration of larger DNA molecules into smaller fragments, which can be carried out physically (for example with ultrasound) or chemically (for example enzymatically).

In accordance with the invention, therefore, a number of novel sequencing vectors is provided which simplify the number of stages before the base-specific degradation reactions to a single restriction and a completing (topping up) labelling reaction. According to this method, no overlapping non-readable area is formed. Further, the subcloning protocol according to the invention results in practically no background or underground clones. A prototype for suitable sequencing plasmids is explained in detail in the following and is called pCSV03.

Production of pCSV03 pGV001 is a 1882 bp derivative of pBR327; it is formed by cleaving pBR327 with HindIII and AvaI, completing (topping up) the protruding ends and automatically linking the blunt ends. pGV001 carries a replication source and B-lactamase gene. The individual EcoRI, ClaI and HindIII cleavage sites lie behind these areas. pCSV03 is formed by the introduction of a chemically synthesised DNA fragment (10 bp ds) into the completed (topped up) ClaI site of pGV001 as shown by the schematic diagram:

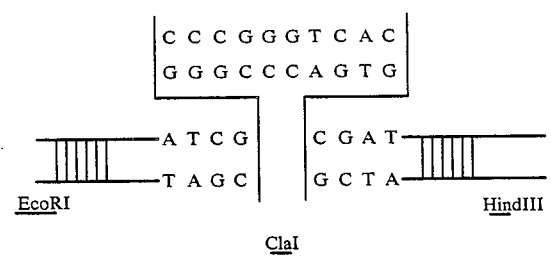

pCSV03 contains individual cleavage sites for EcoRI, SmaI, EcaI (=BstEII) and HindIII.

Cleavage with EcaI (=BstEII) produces a linearised vector molecule with two different protruding 5'-ends.

A completing reaction in the presence of dGTP, dTTp and alpha $^{32}$P-dCTP labels only the left-hand end. Since dATP is missing from the reaction mixture the right-hand end cannot be labelled.

pCSV03 exhibits for a subcloning sequencing the following features:

(1) An EcaI or BstEII cleavage site, which can be individually labelled by a single completing reaction.

(2) An SmaI cleavage site, which overlaps the EcaI site. SmaI can be used as the insertion site with blunt end. Each fragment that is introduced at this site is adjacent to EcaI, so that it can easily be individually labelled on this side.

(3) EcoRI site 23 bp remote from SmaI site, opposite to EcaI. The vector can be cleaved twice with EcoRI and SmaI and used for orienting subcloning of DNA fragments fractionated according to size, and render possible a progressive sequencing; d.f. as follows.

(4) A small (1894 bp) vector treated with phosphatase and linearised with SmaI can readily be preparatively purified on a low-melting agarose gel (2%). A vector purified in this manner produces less than 1% of underground clones as a result of self-linking.

(5) The transformation selection depends on the ampicillin resistance gene.

Subcloning in pCSV03

Subcloning of the pCSV03 may be carried out by the following procedures.

A. Random subcloning (shotgun subcloning):

Fragments with blunt end from restrictions, random restriction products with DNase (i.e. random DNase digests), or DNA exposed to ultrasonic waves are obtained. The dephosphorylated vector is cleaved with SmaI followed by a Litigation reaction and Transformation.

B. Oriented subcloning:

Linking of EcoRI linkers with the DNA molecule to be sequenced is followed by Exposure of the DNA to ultrasonic waves or treatment with DNase and Cleavage with EcoRI. Fractionation on a low-melting agarose gel (2%) and Linking of size fractions with pCSV03 treated with EcoRI-SmaI is followed by Transformation of individual fractions.

Only fragments with an original end can be linked with the vector, since they alone carry a sticky EcoRI end at one side. The opposite side (the blunt end) is adjacent to EcaI. Consequently, different gel fractions form a group of overlapping sequences. As shown below.

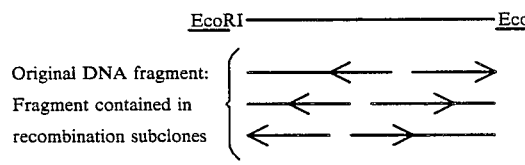

The arrows represent segments sequenced one after the other. Note: A DNA molecule that contains one or more EcoRI sites can be used without the addition of EcoRI linkers. The molecule is circularised before being exposed to ultrasonic waves. EcoRI cleavage must follow exposure to ultrasonic waves.

Sequencing of recombination subclones of pCSV03

The sequencing of recombination subclones of pCSV03 may be carried out by a procedure which entails the following.

1. Colonies are picked out and 1 ml cultures grown overnight.
2. The cells are centrifuged, lysed (for example according to the heating method described by Quigley and Holmes) and clarified.
3. The recombination DNAs are obtained.
4. Cleavage is carried out with BstEII, a commercially available enzyme.
5. Completion is carried out with Klenow polymerase and dGTP, dTTP and alpha $^{32}$P-dCTP.
6. Centrifuging rapidly through Sephadex G50 (1 ml) is carried out.
7. Chemical degradation reactions are initiated.

Production of pCSV31 pCSV31 is produced by cutting pCSV03 with the restriction enzyme SmaI. A chemically synthesized double-stranded DNA-fragment (20 bp) having the following sequence is inserted into the cutting site:

TGACTAAGTCGACTCAGTCA
ACTGATTCAGCTGAGTCAGT

The two labelling sites (b) and (d) differ by two different protruding ends. To sum up, pCSV31 is characterized by the following features:

(1) A SalI-cutting site as the first insertion (a).
(2) A Tth111I-cutting site as labelling site (b).
(3) A Tth111I-cutting site as labelling site (d)
(4) where (b) and (d) differ with respect to their sequence.
(5) A EcoRI-cutting site as insertion site (c).
(6) The ampicillin resistance gene.
(7) A length of less than 2000 base pairs.

Where used above, the following abbreviations have the meanings given below:

| | |
|---|---|
| pBR 327 | plasmid deposited on April 22, 1983 as DSM 2629; see Genes, 9 (1980) 287–305 |
| bp | base pair(s) |
| ds | double-stranded |
| dGTP | deoxyguanosine triphosphate |
| dTTP | deoxythymidine triphosphate |
| dCTP | deoxycytidine triphosphate |
| dATP | deoxyadenosine triphosphate |

We claim:
1. A process for sequencing DNA, which comprises;
A. introducing into the insertion site of a double-stranded vector having
   (a) a first insertion site for foreign DNA that occurs only once in the vector; and
   (b) a first labelling site that occurs only once in the vector selected from the following types:

| | | |
|---|---|---|
| (i) | —X3' | YX+ - |
| | —X+Y+5' | X - or |
| | —X3' | YZ - |
| | —X+Y+5' | Z+ - or |
| (ii) | —X M Z3' | N+Z+ - |
| | —X+M+5' | Z+N X - or |
| | —X M Z3' | N+Y - |
| | —X+M+5' | Z+N Y+ - or |
| (iii) | —X M3' | N X+ - |
| | —X+M+5' | N+X - or |
| | —M X3' | X+N - |

-continued

| —M+X+5' | X N+ - or |
| —X M3' | N Y+ - |
| —X+M+5' | N+Y - or |
| —M X3' | Y+N - |
| —M+X+5' | Y N+ - | in which each of M and N represents a single nucleoside from the group consisting of adenosine, cytidine, guanosine and thymidine, M+ and N+ represent the nucleosides complementary to M and N, M is not the same as N, each of X, Y and Z is at least one nucleoside selected from the group consisting of adenosine, cytidine, guanosine and thymidine, X+, Y+ and Z+ represent the nucleosides complementary to X Y and Z, the nucleosides or nucleoside combinations represented by X, Y and Z are not identical to one another and the insertion site (a) and the labelling site (b) are directly adjacent to each other or are separated from each other by up to 1000 base pairs; the DNA to be sequenced;

B. cutting the labelling site of the cloned hybrid vector; and
C. supplementing the resulting ends of the opened hybrid vector in the presence of DNA polymerase and one or more of the triphosphates dGTP, dTTP, dCTP and dATP, one of the triphosphates being labelled and the hybrid vector is individually labelled; and the labelled and opened hybrid vector is base-specifically degraded and the products of the degradation are analyzed for sequence.

2. A process according to claim 1, wherein there are used as DNA, overlapping DNA fragments which have been obtained by random degradation of a larger DNA molecule.

3. A process for sequencing DNA, which comprises:
A. providing the DNA to be sequenced, wherein each end of the DNA to be sequenced is further provided with a site that corresponds to one of the two insertion sites of a vector having
 (a) a first insertion site for foreign DNA that occurs only once in the vector;
 (b) a first labelling site that occurs only once in the vector selected from the following types:

| (i) | - X3' | YX+ - |
| | - X+Y+5' | X - or |
| | - X3' | YZ - |
| | - X+Y+5' | Z+ - or |
| (ii) | - XMZ3' | N+Z+ - |
| | - X+M+5' | Z+NX - or |
| | - XMZ3' | N+Y - |
| | - X+M+5' | Z+NY+ - or |
| (iii) | - XM3' | NX+ - |
| | - X+M+5' | N+X - or |
| | - MX3' | X+N - |
| | - M+X+5' | XN+ - or |
| | - XM3' | N Y+ - |
| | - X+M+5' | N+Y - or |
| | - MX3' | Y+N - |
| | - M+X+5' | YN+ - | in which each of M and N represents a single nucleoside from the group consisting of adenoside, cytidine, guanosine and thymidine, M+ and N+ represent the nucleosides complementary to M and N, M is not the same as N, each of X, Y and Z is at least one nucleoside selected from the group consisting of adenosine, cytidine, guanosine and thymidine, X+, Y+ and Z+ represent the nucleosides complementary to X Y and Z, the nucleosides or nucleoside combinations represented by X, Y and Z are not identical to one another and the insertion site (a) and the labelling site (b) are directly adjacent to each other or are separated from each other by up to 1000 base pairs; and (c) a second insertion site for foreign DNA and, on cutting, one of the first and second insertion sites accepts protruding ends and the other insertion site blunt ends;

B. cutting the DNA to be sequenced from a fragment wherein the cut DNA to be sequenced can be exchanged for the DNA fragment resulting when the vector is cut at the insertion sites;
C. exchanging the DNA to be sequenced as cut from the provided DNA fragment for the DNA fragment resulting when the vector is cut at the two insertion sites;
D. cloning the hybrid vector formed in step C.;
E. cutting the labelling site of the cloned hybrid vector;
F. supplementing the resulting ends of the opened, hybrid vector in the presence of DNA polymerase and one or more of the triphosphates dGTP, dTTP, dCTP and dATP, one of the triphosphates being labelled, and the hybrid vector is individually labelled; and
G. degrading the labelled, opened hybrid vector base-specifically and the products of the degradation are analyzed for sequence.

4. A process according to claim 3, wherein each end of the DNA to be inserted into the vector and to be sequenced is provided with a site that corresponds to that one of the two insertion sites for protruding ends of the vector and the DNA developed in this manner is then degraded to form fragments with one blunt end and where the other end carries one of the original two sites that correspond to the vector insertion site for protruding ends, and the latter end is cleaved.

5. A process according to claim 3 wherein the DNA to be sequenced has a selection marker.

6. A process for sequencing DNA, which comprises;
A. introducing the DNA to be sequenced into the insertion site of a vector having
 (a) a first insertion site for foreign DNA that occurs only once in the vector;
 (b) a first labelling site that occurs only once in the vector selected from the following types:

| (i) | —X3' | YX+ - |
| | —X+Y+5' | X - or |
| | —X3' | YZ - |
| | —X+Y+5' | Z+ - or |
| (ii) | —X M Z3' | N+Z+ - |
| | —X+M+5' | Z+N X - or |
| | —X M Z3' | N+Y - |
| | —X+M+5' | Z+N Y+ - or |
| (iii) | —X M3' | N X+ - |
| | —X+M+5' | N+X - or |
| | —M X3' | X+N - |
| | —M+X+5' | X N+ - or |
| | —X M3' | N Y+ - |
| | —X+M+5' | N+Y - or |
| | —M X3+ | Y+N - |
| | —M+X+5' | Y N+· | in which each of M and N represents a single nucleoside from the group consisting of adenosine, cytidine, guanosine and thymidine, M+ and N+ represent the nucleosides complementary to M and N, M is not the same as N, each of X, Y and Z is at least one nucleoside selected from the group consisting of adenosine, cytidine, guanosine and thymidine, X+, Y+ and Z+ represent the nucleosides complementary to X Y and Z, the nucleosides or nucleoside combinations represented by X, Y and Z are not identical to one another and the insertion site (a) and the labelling site (b) are directly adjacent to each other or are separated from each other by up to 1000 base pairs; and (c) a second labelling site of the same type as the first labelling site;

B. cloning the hybrid vector formed;
C. cutting the two labelling sites of the cloned hybrid vector;
D. supplementing the two ends of the cut fragment with the incorporated DNA in the presence of DNA polymerase and one or more of the triphosphates dGTP, dTTP, dCTP and dATP, one of the triphosphates being labelled, whereby only one 3' end of the cut fragment is individually labelled; and
E. degrading the labelled cut fragment base-specifically and the products of the degradation are analyzed for sequence.

* * * * *